United States Patent
Eisen et al.

(10) Patent No.: US 6,757,064 B2
(45) Date of Patent: Jun. 29, 2004

(54) DEVICE FOR OPTICALLY SCANNING A MOVING WEB OF MATERIAL AND METHOD FOR ADJUSTING SAID DEVICE

(75) Inventors: Juergen Eisen, Augsburg (DE); Stefan Zott, Gessertshausen (DE)

(73) Assignee: Erhardt + Leimer GmbH, Augsburg (DE)

( * ) Notice: Subject to any disclaimer, the term of this patent is extended or adjusted under 35 U.S.C. 154(b) by 252 days.

(21) Appl. No.: 10/121,155

(22) Filed: Apr. 11, 2002

(65) Prior Publication Data

US 2002/0154306 A1 Oct. 24, 2002

(30) Foreign Application Priority Data

Apr. 18, 2001 (DE) .......................................... 101 18 886

(51) Int. Cl.[7] .............................................. G01N 21/84
(52) U.S. Cl. ........................ 356/429; 356/430; 356/431
(58) Field of Search ................................. 356/429–431

(56) References Cited

U.S. PATENT DOCUMENTS 4,938,601 A    7/1990   Weber

FOREIGN PATENT DOCUMENTS

| DE | 32 00 508 | 9/1982 |
|---|---|---|
| DE | 37 09 500 | 10/1988 |
| DE | 39 06 707 | 9/1990 |
| DE | 39 10 873 | 10/1990 |
| DE | 39 23 521 | 1/1991 |
| DE | 41 00 400 | 7/1992 |
| DE | 42 25 320 | 1/1994 |
| DE | 42 25 319 | 2/1994 |
| DE | 196 33 337 | 2/1998 |
| DE | 196 38 912 | 3/1998 |
| DE | 197 44 938 | 6/1998 |
| DE | 197 58 104 | 7/1999 |
| DE | 199 39 643 | 3/2001 |

Primary Examiner—Frank G. Font
Assistant Examiner—Amanda Merlino
(74) Attorney, Agent, or Firm—Collard & Roe, P.C.

(57) ABSTRACT

A device serves for optically scanning a moving material web. The device is formed by a CCD camera comprising a lens and a CCD receiving element, which is provided with photodiodes. So as to be able to exactly adjust the area of the material web scanned by means of the device, the CCD receiving element can be adjusted transversely in relation to the optical axis of the lens. For adjusting the CCD receiving element, a template with a structure is provided. This structure is detected by the photodiodes, and the signals emitted by the photodiodes act on a controlling device. The controlling device adjusts the CCD receiving element so that it is aligned with the structure of the template.

12 Claims, 2 Drawing Sheets

```
11111111000000001000000110000010100000011
10000100100001011000011010000111100010 00
100110001010100010111000110010001101100 0
111010001111100100101001001110010101100 1
011010010111100110011010100110111001110 1
100111101001111101010101110101101101011
11101101111011101111111
```

DEVICE FOR OPTICALLY SCANNING A MOVING WEB OF MATERIAL AND METHOD FOR ADJUSTING SAID DEVICE

CROSS REFERENCE TO RELATED APPLICATIONS

Applicant claims priority under 35 U.S.C. §119 of German Application No. 101 18 886.2 filed Apr. 18, 2001.

BACKGROUND OF THE INVENTION

1. Field of the Invention

The invention relates to a device for optically scanning a moving web of material. The device is formed by at least one CCD camera directed against the material web. The camera includes a lens and a CCD receiving element scanning an area of the material web. The invention also relates to a method for adjusting the moving web of material.

2. The Prior Art

A device for scanning and analyzing the surface of a moving web of material is known from German Patent No. 37 09 500 C2. This device is formed by a CCD camera, which is directed against the web of material. The CCD camera includes a lens and a CCD receiving element. To completely analyze the surface of a very wide web of material, a plurality of such devices must be mounted next to one another. It is important in this connection that the scanned areas of the CCD receiving elements are coordinated so that they are exactly aligned with each other.

A device for measuring the speed of a jet of fluid and the detected length in a combined manner is known from German Patent No. 32 00 508 C2. From these two measured quantities, it is possible to determine the volume flow over the cross section of the jet. For this purpose, the devices include a receiving element that is formed by a plurality of diodes. Light reflected by the jet of fluid acts upon the diodes via a lens and a beam divider. By displacing the receiving element axially relative to the lens, it is possible to vary the area of the jet of fluid detected by the receiving element and to measure the illuminated area of the fluid.

SUMMARY OF THE INVENTION

An object of the present invention is to provide a device for optically scanning a moving web of material that permits a simple and highly sensitive adjustment of the area scanned by the CCD camera. Furthermore, the aim of the invention is to specify a simple method for adjusting the scanned area.

In accordance with the invention, these and other objects are accomplished by providing a device for optically scanning a moving material web formed by at least one CCD camera directed against the material web. The camera includes a lens and a CCD receiving element scanning an area of the material web. For adjusting the scanning range of the device, a template can be fixed in the area of the plane of the material web. The template has at least one structure extending transversely in relation to the direction of movement of the material web, which is detectable by the CCD camera. The CCD receiving element can be adjusted in relation to the lens transversely to its optical axis by at least one drive. The drive is actively connected with a controlling device responsive to signals from the CCD camera.

The template may include a digital coding detectable by the CCD camera. This coding is formed by a sequence of bits, in which any desired partial sequence of an "n" number of directly successive bits of the sequence supplies a clear n-bit code for the absolute position of the CCD camera along the template.

The device as defined by the invention serves for optically scanning a moving web of material. In particular, the device serves to control the surface of the moving web of material optically so as to detect any weaving, printing and dying defects. The device may also be used to detect the marginal edge or a printed marking of the web of material in order to detect the course along which the material web is moving. The device is formed by at least one CCD camera that is directed against the web of material and includes a lens and a CCD receiving element. Because the web of material is moving past the camera, the CCD receiving element may take the form of a line receiving element, with all light-sensitive photodiodes in the element arranged next to each other. By generating a plurality of images of the line that are offset in terms of time, it is possible to obtain a complete image of the surface of the web of material due to the movement of the material web. In particular in connection with wide webs of material, the range scanned by one single CCD camera is not adequate for detecting the surface of the web of material over the entire width of the material. Several CCD cameras generally are employed for that reason that are distributed over the width of the web of material. These CCD cameras have to be coordinated with each other. Specifically, their scanning ranges will be aligned with one another, so that the individual CCD cameras combined will supply a through-extending scanning line extending transversely in relation to the direction in which the web is running. In this way it is assured that the images generated by the individual CCD cameras can be correctly assembled to obtain an overall image, so that defects located in the area of transition between two CCD cameras can be correctly detected as well; so that the CCD cameras may scan the web of material without any gaps, it is important that the scanning ranges are correctly adjusted to one another, with a minor overlap, and to a narrow marking illuminated along the web of material. But even if only one single CCD camera is used, it is important that the CCD camera be positioned so that the area of the material web illuminated along a line is located within the range scanned by this CCD camera. To permit very fine adjustment of the areas of the web scanned by the CCD cameras, in accordance with the invention, the CCD receiving element of the CCD camera is adjusted transversely to the optical axis of the lens of the camera. In this way, adjusting the relatively lightweight CCD receiving element alone is sufficient without also having to drive the lens along with the help of an automatically focusing ("autofocus") control device that may be installed. Because the lens of the CCD camera is not driven with the CCD receiving element, the CCD receiving element will be shifted away from (or to the outside of) the optical axis of the lens; however, this shifting is acceptable, particularly for finely adjusting the scanning range. So that the CCD cameras can be correctly aligned, a template can be fixed at the level of the plane of the material web with at least one structure aligned transversely to the direction of movement of the material web. In particular, the template is provided with a line extending transversely in relation to the direction in which the web of material is moving. This line supplies an adequately high optical contrast vis-à-vis the rest of the template, so that this line can be easily detected by the CCD camera. So that the adjustment process can be carried out in the simplest manner possible, the CCD receiving element is set by drives that are actively connected with a controlling device. This controlling device is influenced or regulated by the signals emitted by the CCD receiving elements. In this way, the CCD receiving elements are automatically adjusted to the structure on the template, so that adjustments are executed quickly and always with a constantly high quality.

So as to achieve an exact alignment of the scanning ranges of the CCD camera, it is sufficient to displace the CCD receiving element in the direction in which the material web is running, as well as transversely to the optical axis of the lens. Any additional transverse displacement of the CCD receiving element relative to the moving direction of the material web is unnecessary because these alignment errors can be taken into account by selecting a suitable amount of overlap between the CCD cameras.

So that the individual image lines generated by the CCD receiving elements can be easily assembled to form an image, it is important that the receiving elements be aligned in parallel with one another. However, the overall structure of the holding devices for mounting the CCD cameras contain manufacturing tolerances with respect to the alignment of the receiving line of the CCD receiving element. Such tolerances lead to a deviation of the alignment from the ideal parallelism that is relevant to the evaluation of the received image. It is therefore favorable if the CCD receiving element is supported so that it can be rotated about an axis of rotation that extends approximately parallel to the optical axis of the lens. Turning the CCD receiving element by one to three degrees generally suffices because the aforementioned manufacturing tolerances are minor. This arrangement enables the light source to emit a particularly narrow band of light, yet nonetheless assures that the CCD cameras will detect only the illuminated section of the material web.

So that the required adjustability of the CCD receiving element can be realized in the simplest possible way, it is advantageous if the CCD receiving element is mounted on a revolving table that is rotatably supported on a sliding carriage. In this way, the CCD receiving element can be both rotated and displaced transversely in relation to the optical axis in a very simple manner while nonetheless keeping the mechanical expenditure at a low level.

To achieve a precise displacement or turning of the CCD receiving element, it is important that the revolving table or the sliding carriage be driven with as little play as possible. Since the driving of the revolving table or sliding carriage requires gears that are always subject to play, it is favorable if such play is excluded by means of at least one spring engaging the revolving table or the sliding carriage.

So as to assure that the revolving table and the sliding carriage are driven in a simple and precise way, it is favorable if two spindle nuts engage the revolving table. Each spindle nut is engaged by a threaded spindle driven by a servo-motor, preferably an adjusting or stepping motor. By synchronously turning the two threaded spindles in the same sense of rotation, the sliding carriage is displaced along a guide without rotation of the revolving table. On the other hand, by synchronously turning the two threaded spindles in opposite directions of rotation, the revolving table is turned without moving the sliding carriage. When the revolving table is turned, the threaded spindles do not perform a pure sliding movement but are slightly pivoted at the same time. Because the required angles of rotation for turning the revolving table are very small, to simplify the structure of the device, the threaded spindle may be designed to pivot to a limited extent in the nut of the spindle or in the servo-motor. In this way, no additional means is necessary to compensate for the pivotal movement of the threaded spindle. Preferably, the threaded spindle engages the nut of the spindle or the servo-motor with play, so that the required pivotal movement of the threaded spindle can be absorbed by the spindle. By biasing the revolving table or sliding carriage in one direction with a spring in the proposed manner, such play will have no bearing on the precision of the movement of the CCD receiving element.

So that the scanning ranges of the individual CCD cameras can be adjusted to each other with a slight, preset amount of overlap, it is important to detect the absolute position of the individual CCD cameras on the web of material. For this purpose, the template is provided with a digital coding that is detected by the CCD receiving element. The coding consists of a sequence of bits that are scanned by the CCD receiving element. Because too much time and effort is required for start-up by first focusing the individual CCD cameras on a zero point of the measurement range, the coding contains an "n" number of bit codes that clearly reflect the absolute position of the CCD receiving element. It is important in this connection that any desired partial sequence of an "n" number of successive bits directly following each other supplies a clear n-bit code. In this case, reading of the "n" number of bits can be started at any desired point within the sequence while nonetheless assuring that the code that has been so read is suitable for clearly determining the position of the CCD receiving element. In this way, detecting the "n" number of successive bits of the sequence is sufficient to determine the position, so that only a very small portion of the sequence of bits has to be evaluated.

The method as defined by the invention has been successfully tested for adjusting the device specified above for optically scanning a moving web of material by means of at least one CCD receiving element. In this process, a template is first fixed in the area of the plane of the material web. The template has a structure that extends transversely in relation to the direction in which the web of material is moving. This structure can be detected by the CCD receiving element. The structure is preferably formed by a printed line that extends crosswise in relation to the direction in which the material web is moving. The photodiodes of the CCD receiving element generate signals that are dependent upon whether these photodiodes detect the structure or an area of the template located next to the structure. For example, the structure may be formed by a white line that is imprinted on an otherwise black template. The light reflected by the white line generates in the respective photodiodes a photo-signal, whereas the black surface of the template results substantially in a zero level on the receiver diodes. The signals generated by the photodiodes are evaluated as to which ones of the photodiodes detect the structure and which ones detect the areas located next to the structure. Depending on the result of the evaluation, the CCD receiving element is adjusted so that it is aligned with the structure. This adjustment is carried out automatically without any activity required by the operating personnel. The adjustment process is carried out rapidly with no change in the high quality of the adjustment. After the adjustment has been made, the CCD receiving element is maintained in the adjusted position. With the CCD receiving element in the adjusted position, the template may be subsequently removed in order for the CCD receiving element to scan surface structures of the moving web of material.

So that the CCD receiving element can be adjusted as precisely as possible, it is necessary to provide the structure applied to the template with a relatively narrow configuration. The consequence thereof, however, is that before the adjustment process starts, the structure most likely will be disposed completely outside of the detection range of the CCD receiving element. In that case, it is advantageous if the CCD receiving element is first displaced transversely to the structure until it is located within the scanning range of at least one of the photodiodes. Following this rough adjustment, clues at least can be obtained from the signals generated by the photodiodes about the possible configuration of the structure of the template in relation to the CCD receiving elements. Such clues are important for the further adjustment of the CCD receiving element. In particular, the point where the structure on the template intersects the scanning line of the CCD receiving element can be determined by evaluating the position of those photodiodes within the CCD receiving element that supply a corresponding active signal. Based on the number of the photodiodes that supply an active signal, it is then possible to deduce the angle that is enclosed by the two aforementioned lines between each other.

To obtain an adjustment algorithm that is simple yet nonetheless efficient, it is favorable if the CCD receiving element is turned and displaced so that the number of photodiodes detecting the structure of the template is maximized in each case. This maximization specification generally suffices for aligning the CCD receiving elements with the structure with a finite number of steps. The CCD receiving element is preferably turned and displaced in an alternating manner so that the two modes of adjustment will exert the smallest possible influence on each other. By rotating the CCD receiving element, the greater the number of receiving elements detecting the structure, the smaller the angle between the two receiving elements will be. If the axis of rotation of the CCD receiving element fails to coincide with the range of detection of the CCD receiving element, rotating the CCD receiving element will result in an apparent displacement of the structure in relation to the photodiodes. Such an apparent shift is corrected between each two rotations by a corresponding displacement of the CCD receiving elements.

Finally, to improve the efficiency of the adjustment algorithm, it is advantageous if the CCD receiving element is displaced so that the template structure extends approximately symmetrically through the axis of rotation. If the CCD receiving element is arranged approximately symmetrically with respect to the axis of rotation, it is generally sufficient if the axis of rotation is shifted so that the photodiodes supplying an active signal will be distributed approximately symmetrically around the center photodiode of the CCD receiving element. What is achieved with this measure is that the axis of rotation is approximately located within the range of detection of the CCD receiving element. In turn, the consequence thereof is that after the CCD receiving element has been turned, it has to be displaced only very slightly, so that the adjustment process will lead to an overall optimal adjustment of the CCD receiving element in just a few adjustment steps. The CCD receiving element may also be turned and displaced at the same time. In that case, maximizing of the number of photodiodes detecting the structure will have a bearing substantially only on the rotation of the CCD receiving element. Any detected asymmetry of the signals generated by the photodiodes will effect a displacement of the CCD element that will compensate for such rotation.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENTS

Figure 1:
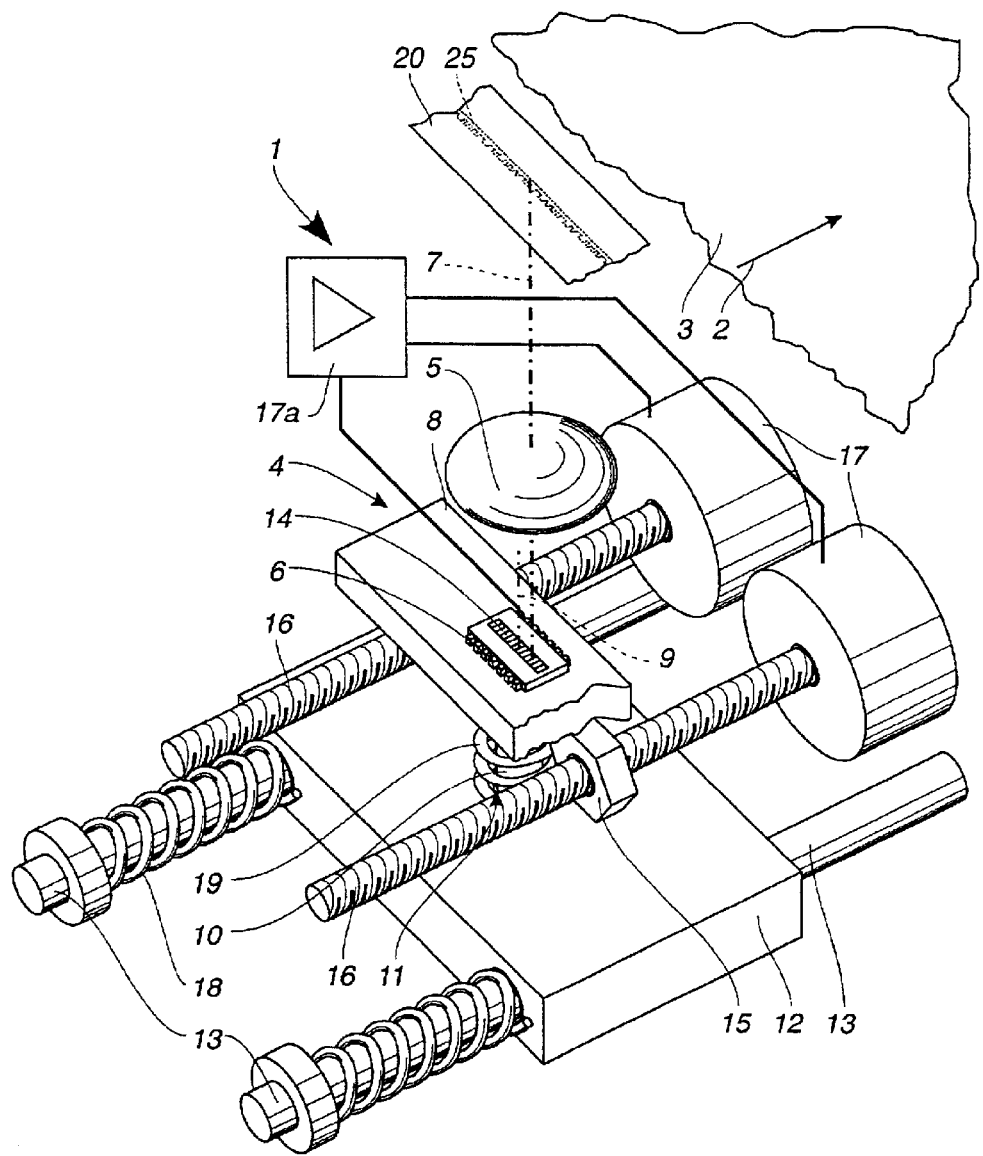
FIG. 1 is a schematic three-dimensional representation of a device for optically scanning a moving web of material.

Referring now in detail to the drawings and, in particular, FIG. 1 is a three-dimensional representation of a device 1 for optically scanning a material web 3 moving in the direction 2. Device 1 includes a charge-coupled device (CCD) camera 4 that is formed by a lens 5 and a CCD receiving element 6. For clarity, lens 5 is shown only as a simple lens, and CCD receiving element 6 is shown in the form of a chip having light sensitive diodes 14. Lens 5, of course, includes a plurality of lenses successively connected one after the other, which are supported in a suitable mounting means. Lens 5 can be displaced in the direction of an optical axis 7 to permit focusing of the image on CCD receiving element 6.

CCD receiving element 6 is supported on a revolving table 8 shown broken away in FIG. 1. The table revolves around rotation axis 9 aligned parallel with optical axis 7 of lens 5. On the underside, revolving table 8 has a pivot pin 10 that is supported in a rotational bearing 11 of a sliding carriage 12.

Sliding carriage 12 is supported on two guide rails 13 so that it can be displaced along rails 13 transversely to optical axis 7 of lens 5 in the direction 2 in which material web 3 is moving. In this way, CCD receiving element 6 can be turned around rotational axis 9 and displaced along guide rails 13. CCD receiving element 6 is aligned so that the line of light-sensitive photodiodes 14 is arranged approximately perpendicular to guide rails 13. To turn and displace CCD receiving element 6, a spindle nut 15 is mounted on revolving table 8 on each of the two sides of pivot pin 10. Each spindle nut 15 is engaged by a threaded spindle 16. Each of the threaded spindles is rotationally driven by a servo-motor 17. Servo-motor 17 is preferably a stepping motor, whereby an auxiliary servo-motor can be alternatively employed as well.

Turning revolving table 8 around rotation axis 9 pivots spindle nuts 15. Accordingly, the two threaded spindles 16 have to be pivotally-mounted as well. For that purpose, the threads of the two threaded spindles 16 are provided with an amount of play in relation to spindle nuts 15 or to servomotors 17 that permits threaded spindles 16 to be pivoted to a minor extent. As a result, revolving table 8 can be turned only by a minor angle of rotation as well; however, such limited rotation is sufficient to compensate for manufacturing tolerances of device 1 or CCD receiving element 6. The resulting device is particularly simple and compact.

In order to compensate for the play caused by threaded spindles 16, guide rails 13 have springs 18 supported thereon which apply pressure in one direction to sliding carriage 12. Furthermore, sliding carriage 12 has a torsion spring 19 mounted and supported thereon, which engages revolving table 8. These two springs 18 and 19 press sliding carriage 12 and revolving table 8 in one direction to the extent permitted by the play of threaded spindles 16. In this way, sliding carriage 12 and revolving table 8 assume a preset position with threaded spindles 16 being in any position, so that play of threaded spindles 16 is compensated.

To adjust CCD receiving element 6, a template 20 is first fixed-in the area of the level of the material web. Template 20 contains a structure 25 that can be detected by photodiodes 14. Servo-drives 17 are actively connected to a controlling device 17a, which is responsive to CCD receiving element 6. For this purpose, controlling device 17a determines the number of photodiodes 14 detecting structure 25 of template 20. This number is maximized by controlling the two servo-drives 17 to rotate in opposite directions. Furthermore, the controlling device 17a determines the number of those photodiodes 14 that represents the center of all of the photodiodes 14 that generate an active signal. The number of the photodiodes 14 so found is compared with the number of the center photodiode 14 of CCD receiving element 6. The difference resulting from this comparison is then used as a control signal for adjusting the two servo-drives 17 in the same sense or direction.

To obtain a control algorithm that is as efficient as possible, CCD receiving element 8 is mounted on revolving table 8 so that its center photodiode 14 will be located as closely as possible to axis of rotation 9 of revolving table 8. The two control signals generated by controlling device 17a are generated simply by determining the numbers of those photodiodes 14 that are located in the area of a bright-to-dark zone of transition. Based on the two numbers, the required control signals may be generated by simply forming the difference and mean values.

Figures 2, 3:
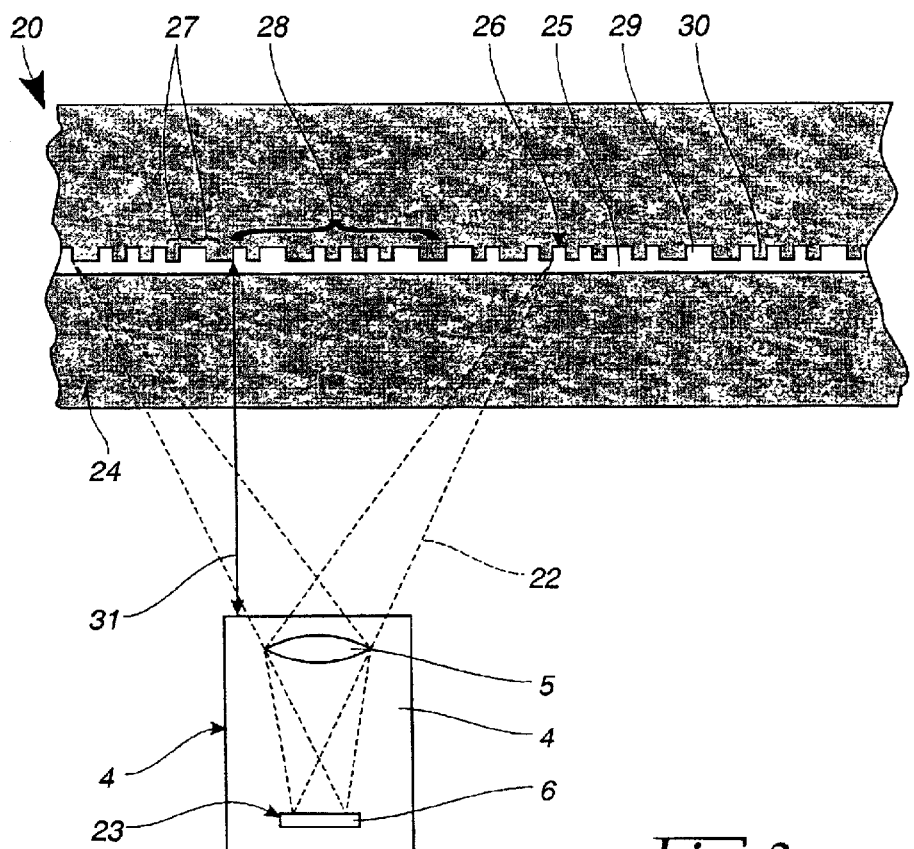
FIG. 2 shows a portion of a template for adjusting the position of a CCD camera.
FIG. 3 shows a code of the template according to FIG. 2.

FIG. 2 shows template 20 for adjusting the CCD camera 4. Template 20 is designed in the form of a ruler. The surface 24 of this ruler is dyed substantially black. Template 20 has a white bar 25 that can be used for balancing the brightness of CCD camera 4 and for aligning CCD receiving element 6. White bar 25 reflects light 22 which generates a photosignal in the sensors 23. Black surface 24 of template 20 results in a substantially zero level on the sensors. Template 20 is also provided with a coding 26 consisting of individual bits 27. Coding 26 is designed so that eight successive bits 27 result in a clear code 28. The clearness (or unambiguity) of code 28 assures that the absolute position of CCD camera 4 along template 20 can be determined by reading eight successive bits 27. So as to be able to determine in addition to the individual bits 27 the width of each bit 27, each individual bit 27 is "manchester"-coded, so that each bit includes a white area 29 and a black area 30. The sequence "black area 30–white area 29" means a 0-bit, and the sequence "white area 29–black area 30" means a 1-bit. Thus it is possible to correctly detect the coding 26 independently of the distance 31 of the subject 21 from device 20, and independently of the focal length of lens 5.

FIG. 3 shows coding 28 in the form of a 0-1 representation of individual bits 27. This coding 28 is structured so that each sequence of eight successive bits 27 supplies a clear, unambiguous 8-bit code that can be used to determine position.

Accordingly, while only a single embodiment of the present invention has been shown and described, it is apparent that many changes and modifications may be made thereunto without departing from the spirit and scope of the invention.

What is claimed is:

1. A device for optically scanning a material web moving in a direction in a plane comprising:
   (a) at least one CCD camera directed at the material web comprising a lens having an optical axis and a CCD receiving element for scanning an area of the material web and generating signals from scanning the web;
   (b) a template disposed in the plane of the web for adjusting a scanning range of the device, said template having at least one structure extending transversely to the moving direction of the web and being detectable by the CCD camera;
   (c) at least one drive coupled to said CCD camera for adjusting the CCD receiving element transversely to the optical axis of the lens; and
   (d) a controlling device connected to said drive for controlling the drive in response to the signals from the CCD camera.

2. The device according to claim 1 wherein the CCD receiving device is mounted to be displaced in the moving direction of the web and transversely in relation to the optical axis of the lens.

3. The device according to claim 1 wherein the CCD receiving device is mounted for rotation around an axis of rotation approximately parallel to the optical axis of the lens.

4. The device according to claim 1 further comprising a sliding carriage and a revolving table rotatably mounted on said sliding carriage, the CCD receiving element being mounted on said revolving table.

5. The device according to claim 4 further comprising at least one spring biasing said sliding carriage in one direction.

6. The device according to claim 4 further comprising at least one spring biasing said revolving table in one direction.

7. The device according to claim 4 wherein said at least one drive comprises a servo-motor and the device further comprises two spindle nuts engaging said revolving table, each spindle nut being engaged by a threaded spindle driven by said servo-motor, each threaded spindle being capable of pivoting in the spindle nut and in the servo-motor.

8. The device according to claim 1 wherein said template comprises a digital coding detectable by said CCD camera, said coding comprising a sequence of bits wherein any selected partial sequence of n directly successive bits of the sequence supplies an unambiguous n-bit code for determining the position of the CCD camera along the template.

9. A method for adjusting a device for optically scanning a material web moving in a direction in a plane, said device having at least one CCD receiving element comprising photodiodes, each photodiode having a scanning range, which comprises the steps of:
   (a) positioning in the plane of the web a template having at least one structure extending transversely to the moving direction of the web;
   (b) detecting said structure by the photodiodes to generate signals; and
   (c) adjusting the position of the CCD receiving element to align with the structure in response to the signals.

10. The method according to claim 9 wherein the CCD receiving element is first displaced transversely in relation to the structure so that the structure is located in the scanning range of at least one of the photodiodes.

11. The method according to claim 9 wherein the CCD element is rotatably mounted around an axis of rotation and positioned to maximize the number of photodiodes detecting the structure.

12. The method according to claim 11 wherein the CCD element is positioned so that the photodiodes detecting the structure extend approximately symmetrically around the axis of rotation.

* * * * *